United States Patent
Kargar et al.

(10) Patent No.: US 8,983,158 B2
(45) Date of Patent: Mar. 17, 2015

(54) SYSTEM FOR PERFORMING CORONARY DIGITAL SUBTRACTION ANGIOGRAPHY (DSA)

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1060 days.

(21) Appl. No.: 12/750,922

(22) Filed: Mar. 31, 2010

(65) Prior Publication Data

US 2011/0026790 A1    Feb. 3, 2011

Related U.S. Application Data

(60) Provisional application No. 61/230,263, filed on Jul. 31, 2009.

(51) Int. Cl.
| | |
|---|---|
| G06K 9/00 | (2006.01) |
| A61B 6/00 | (2006.01) |
| A61B 5/02 | (2006.01) |
| G06T 5/50 | (2006.01) |
| A61B 5/00 | (2006.01) |

(52) U.S. Cl.
CPC ............. *A61B 6/481* (2013.01); *A61B 5/02007* (2013.01); *A61B 5/7289* (2013.01); *A61B 6/503* (2013.01); *A61B 6/504* (2013.01); *A61B 6/541* (2013.01); *G06T 5/50* (2013.01); *G06T 2207/10081* (2013.01); *G06T 2207/10088* (2013.01); *G06T 2207/20224* (2013.01); *G06T 2207/30048* (2013.01)
USPC ........................................................ 382/130

(58) Field of Classification Search
None
See application file for complete search history.

(56) References Cited

U.S. PATENT DOCUMENTS

| | | | | |
|---|---|---|---|---|
| 4,878,115 | A * | 10/1989 | Elion | 378/98.5 |
| 6,556,695 | B1 | 4/2003 | Packer et al. | |
| 2008/0194944 | A1* | 8/2008 | Edelman | 600/420 |
| 2009/0297004 | A1* | 12/2009 | Baumgart | 382/130 |

OTHER PUBLICATIONS http://en.wikipedia.org/wiki/Digital_subtraction_angiography.
http://en.wikipedia.org/wiki/Electrocardiography.
http://en.wikipedia.org/wiki/Fluoroscopy.

* cited by examiner

*Primary Examiner* — Neal Sereboff

(57) ABSTRACT

An image data subtraction system receives an electrical signal representing a heart cycle electrical waveform during multiple heart cycles and acquires data representing a first image set comprising multiple temporally sequential individual mask images of vessels of a portion of patient anatomy during the multiple heart cycles in the absence of a contrast agent. The system acquires data representing a second image set comprising a multiple temporally sequential individual contrast enhanced images of vessels of the portion of patient anatomy during the multiple heart cycles in the presence of a contrast agent. An image data processor automatically uses the electrical signal to identify temporally corresponding pairs of images comprising a mask image and a contrast enhanced image acquired substantially at a same point within a heart cycle. The image data processor, for the corresponding pairs, automatically subtracts data representing a mask image of a corresponding pair from a contrast enhanced image of the corresponding pair, to provide subtracted images.

11 Claims, 7 Drawing Sheets

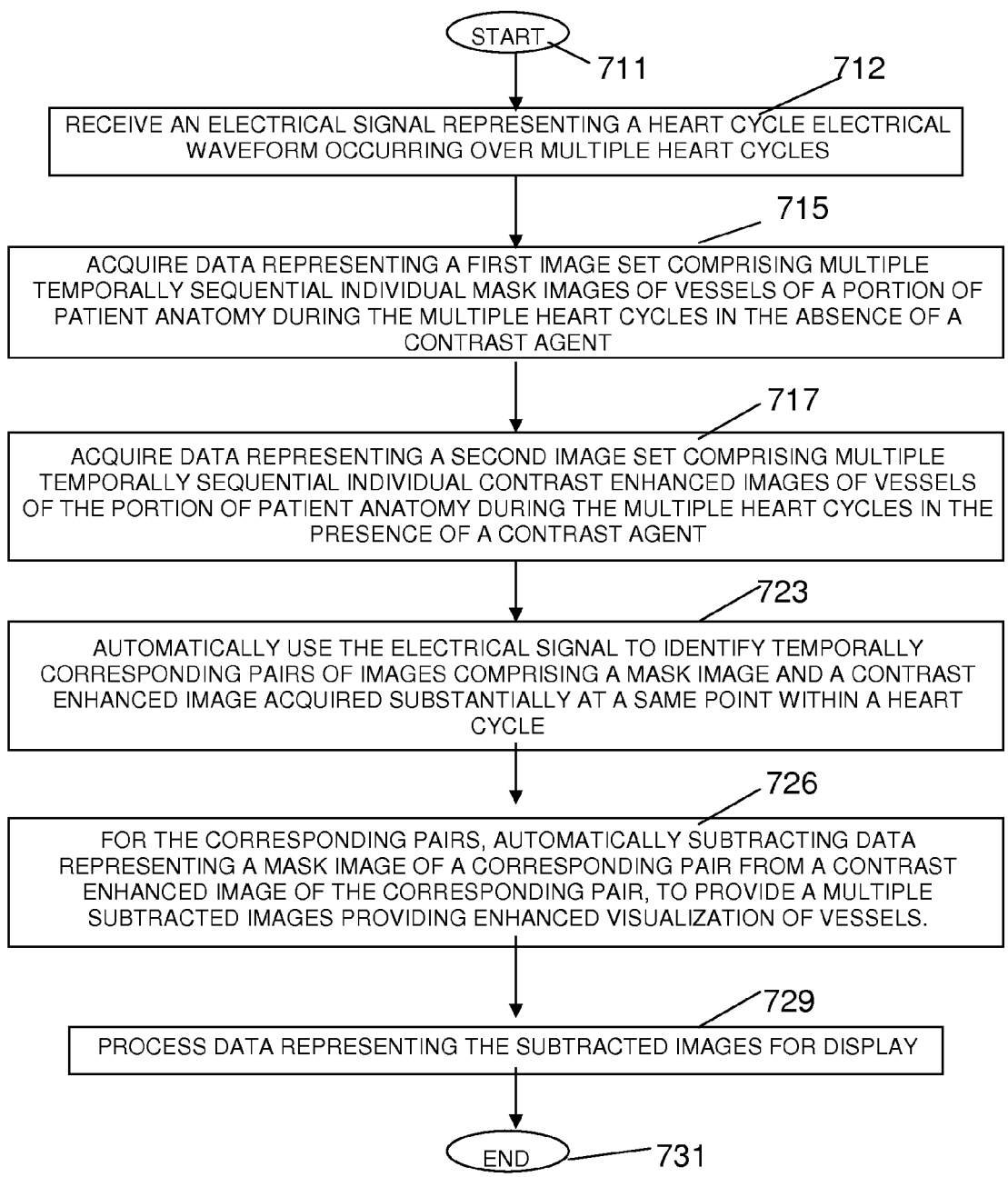

US 8,983,158 B2

SYSTEM FOR PERFORMING CORONARY DIGITAL SUBTRACTION ANGIOGRAPHY (DSA)

This is a non-provisional application of provisional application Ser. No. 61/230,263 filed 31 Jul., 2009, by S. Kargar et al.

FIELD OF THE INVENTION

This invention concerns an image data subtraction system to enhance visualization of vessels subject to movement by identifying and subtracting temporally corresponding pairs of images comprising a mask image and a contrast enhanced image acquired substantially at a same point within a heart cycle.

BACKGROUND OF THE INVENTION

Known imaging systems either fail to perform Digital Subtraction Angiography for coronary vessels or provide flawed images of limited value. Known systems fail to perform DSA in interventional cardiology to provide clear, motion artifact free images of blood vessels of the heart. A system according to invention principles performs Digital Subtraction Angiography of coronary vessels to provide clear, motion artifact free images of blood vessels of the heart and addresses these deficiencies and related problems.

SUMMARY OF THE INVENTION

A system performs Digital Subtraction Angiography of coronary vessels, for example, to provide clear, motion artifact free images of blood vessels of the heart. An image data subtraction system enhances visualization of vessels subject to movement using an interface for receiving an electrical signal representing a heart cycle electrical waveform during a multiple heart cycles. An imaging system acquires data representing a first image set comprising multiple temporally sequential individual mask images of vessels of a portion of patient anatomy during the multiple heart cycles in the absence of a contrast agent. The imaging system acquires data representing a second image set comprising a multiple temporally sequential individual contrast enhanced images of vessels of the portion of patient anatomy during the multiple heart cycles in the presence of a contrast agent. An image data processor automatically uses the electrical signal to identify temporally corresponding pairs of images comprising a mask image and a contrast enhanced image acquired substantially at a same point within a heart cycle. The image data processor, for the corresponding pairs, automatically subtracts data representing a mask image of a corresponding pair from a contrast enhanced image of the corresponding pair, to provide a multiple subtracted images providing enhanced visualization of vessels.

BRIEF DESCRIPTION OF THE DRAWING

FIG. 7 shows a flowchart of a process used by an image data subtraction system enhancing visualization of vessels subject to movement, according to invention principles.

DETAILED DESCRIPTION OF THE INVENTION

A system according to invention principles performs Digital Subtraction Angiography of coronary vessels to provide clear, motion artifact free images of blood vessels of the heart by acquiring a sequence of mask images. A sequence of mask images is acquired before injecting a contrast agent into patient coronary heart vessels and concurrently with acquisition of ECG (Electrocardiogram) information for one or more sequential heart cycles. A mask image is an image of static background detail of anatomy acquired without injection of a contrast agent. A mask image is subtracted from a corresponding image of the same portion of anatomy following injection of a contrast agent, to provide a DSA (Digitally Subtracted Angiography) image with static background eliminated to enhance visualization of contrast agent conveying vessels.

Figure 1:
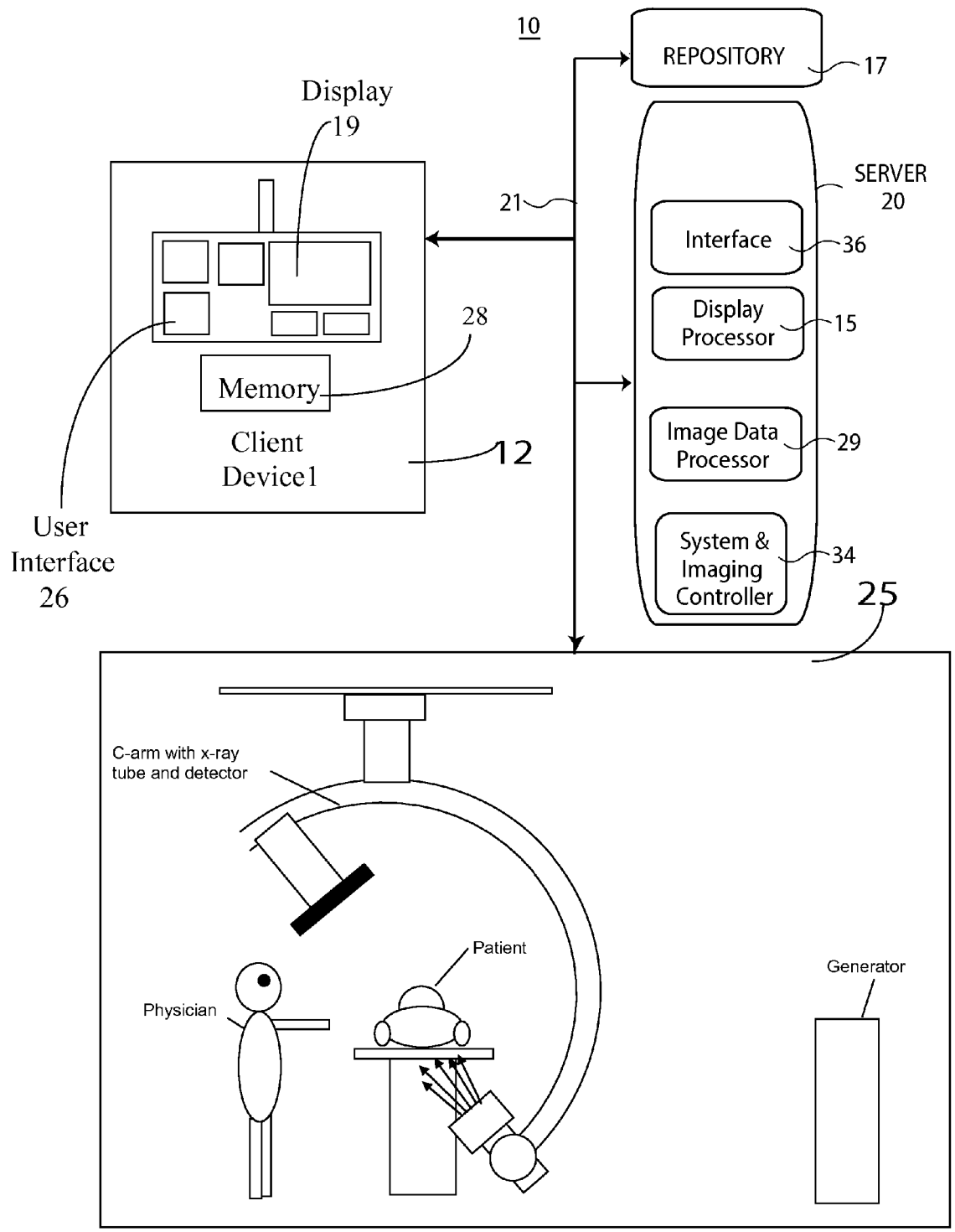
FIG. 1 shows an image data subtraction system enhancing visualization of vessels subject to movement, according to invention principles.

FIG. 1 shows an image data subtraction system 10 enhancing visualization of vessels subject to movement. System 10 includes one or more processing devices (e.g., workstations or portable devices such as notebooks, Personal Digital Assistants, phones) 12 that individually include a user interface control device 26 such as a keyboard, mouse, touchscreen, voice data entry and interpretation device and memory 28. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. X-ray modality system 25 comprises a C-arm X-ray radiation source and detector device rotating about a patient table and an associated electrical generator for providing electrical power for the X-ray radiation system. The display images are generated in response to predetermined user (e.g., physician) specific preferences. At least one repository 17 stores medical image studies for multiple patients in DICOM compatible (or other) data format. A medical image study individually includes multiple image series of a patient anatomical portion which in turn individually include multiple images. Server 20 includes interface 36, display processor 15, image data processor 29 and system and imaging controller 34. Display processor 15 provides data representing display images comprising a Graphical User Interface (GUI) for presentation on display 19 of processing device 12. Imaging controller 34 controls operation of imaging device 25 in response to user commands entered via user interface 26. In alternative arrangements, one or more of the units in server 20 may be located in device 12 or in another device connected to network 2l.

Image data processor 29 processes images acquired by imaging device 25 to provide DSA images for use in Angiography (catheterization and stent manipulation) or other medical procedure to enhance vessel visualization. Interface 36 receives an electrical signal representing a heart cycle electrical waveform during at least one heart cycle. Imaging system 25 acquires data representing a first image set comprising multiple temporally sequential individual mask images of vessels of a portion of patient anatomy during the at least one heart cycle in the absence of a contrast agent. Imaging system 25 also acquires data representing a second image set comprising multiple temporally sequential individual contrast enhanced images of vessels of the portion of patient anatomy during the at least one heart cycle in the presence of a contrast agent. Image data processor 29 automatically uses the electrical signal to identify temporally corresponding pairs of images comprising a mask image and a contrast enhanced image acquired substantially at a same point within a heart cycle. For the corresponding pairs, processor 29 automatically subtracts data representing a mask image of a corresponding pair from a contrast enhanced image of the corresponding pair, to provide multiple subtracted images providing enhanced visualization of vessels.

Figure 2:
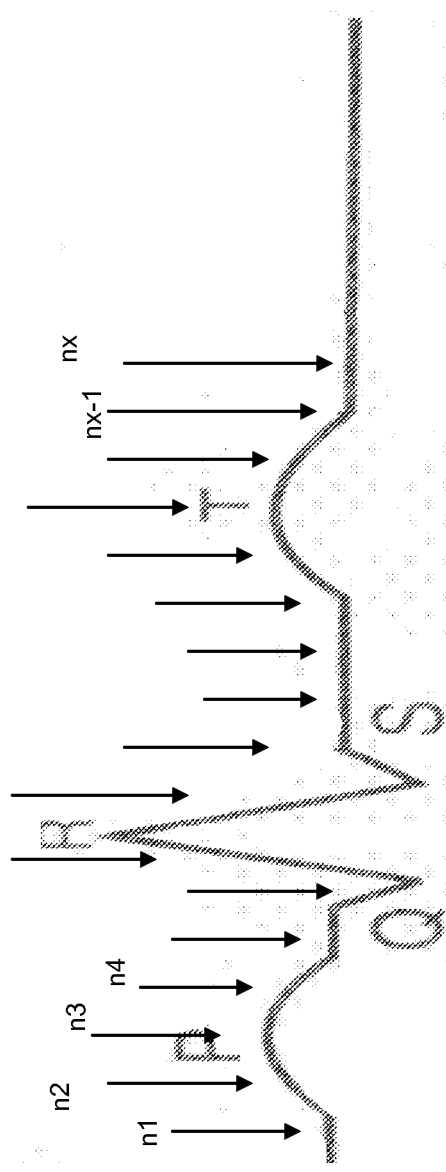
FIG. 2 shows an electrical signal representing a heart cycle electrical waveform indicating temporally sequential image acquisition points in the cycle, according to invention principles.

FIG. 2 shows an electrical signal representing a heart cycle electrical waveform. FIG. 2 indicates temporally sequential image acquisition points in the cycle. Specifically, corresponding pairs of images comprising a mask image and a contrast enhanced image are acquired substantially at the same point within a heart cycle such as point n1, n2, n3, n4 . . . nx−1 or nx, for example.

Figure 3:
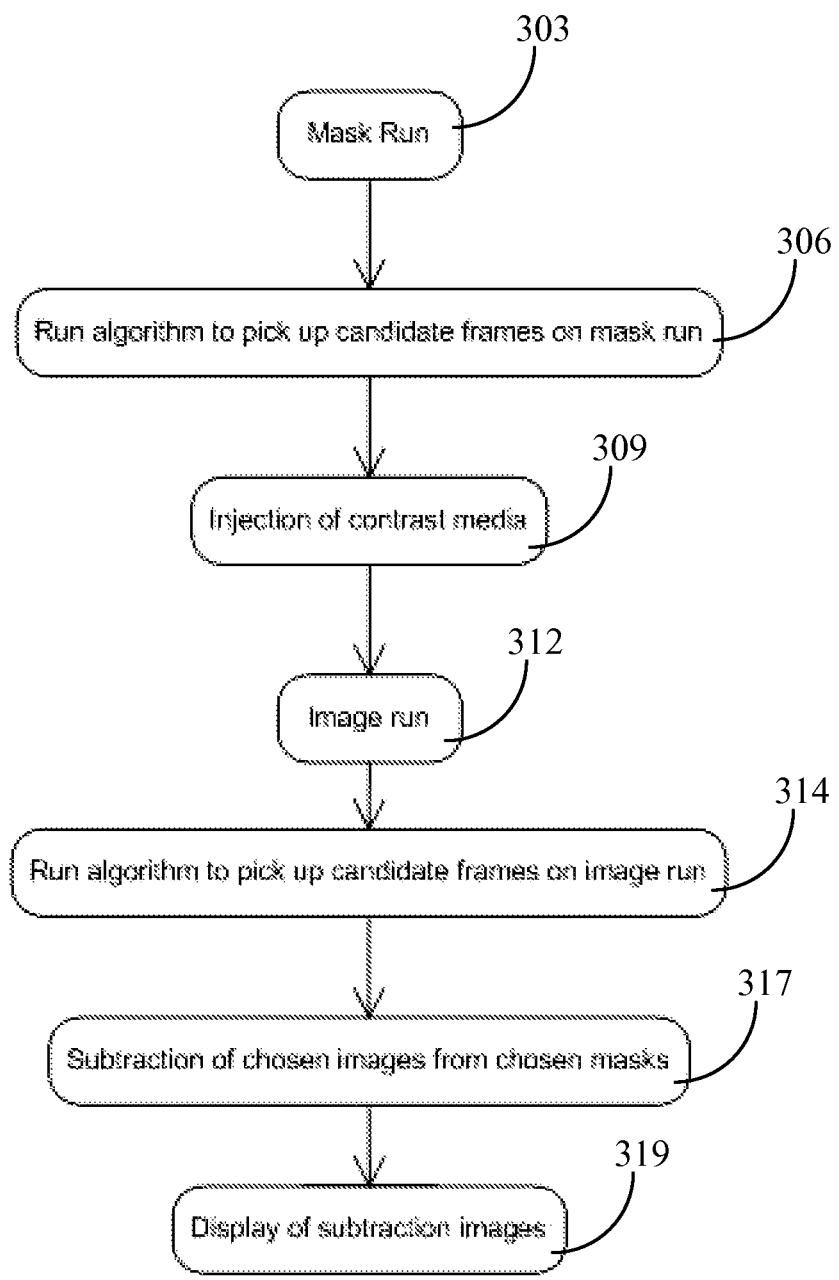
FIG. 3 shows a flowchart of a process performed by an image data subtraction system enhancing visualization of vessels, according to invention principles.

FIG. 3 shows a flowchart of a process performed by image data subtraction system 10 enhancing visualization of vessels. In step 303 imaging system 25 (FIG. 1) acquires data representing a first image set comprising multiple temporally sequential individual mask images of vessels of a portion of patient anatomy during at least one heart cycle in the absence of a contrast agent. In step 306, image data processor 29 identifies and selects candidate mask images. In step 312 following injection of a contrast agent in step 309, imaging system 25 acquires data representing a second image set comprising multiple temporally sequential individual contrast enhanced images of vessels of the portion of patient anatomy during the at least one heart cycle in the presence of a contrast agent. Image data processor 29 in step 314, identifies and selects candidate contrast enhanced images temporally corresponding to the selected mask images to provide temporally corresponding pairs of images comprising a mask image and a contrast enhanced image acquired substantially at a same point within a heart cycle. Processor 29 in step 317, for the corresponding pairs, automatically subtracts data representing a mask image of a corresponding pair from a contrast enhanced image of the corresponding pair, to provide multiple subtracted images offering enhanced visualization of vessels. Display 19 in step 319 presents the subtracted images for viewing by a user.

Figure 4:
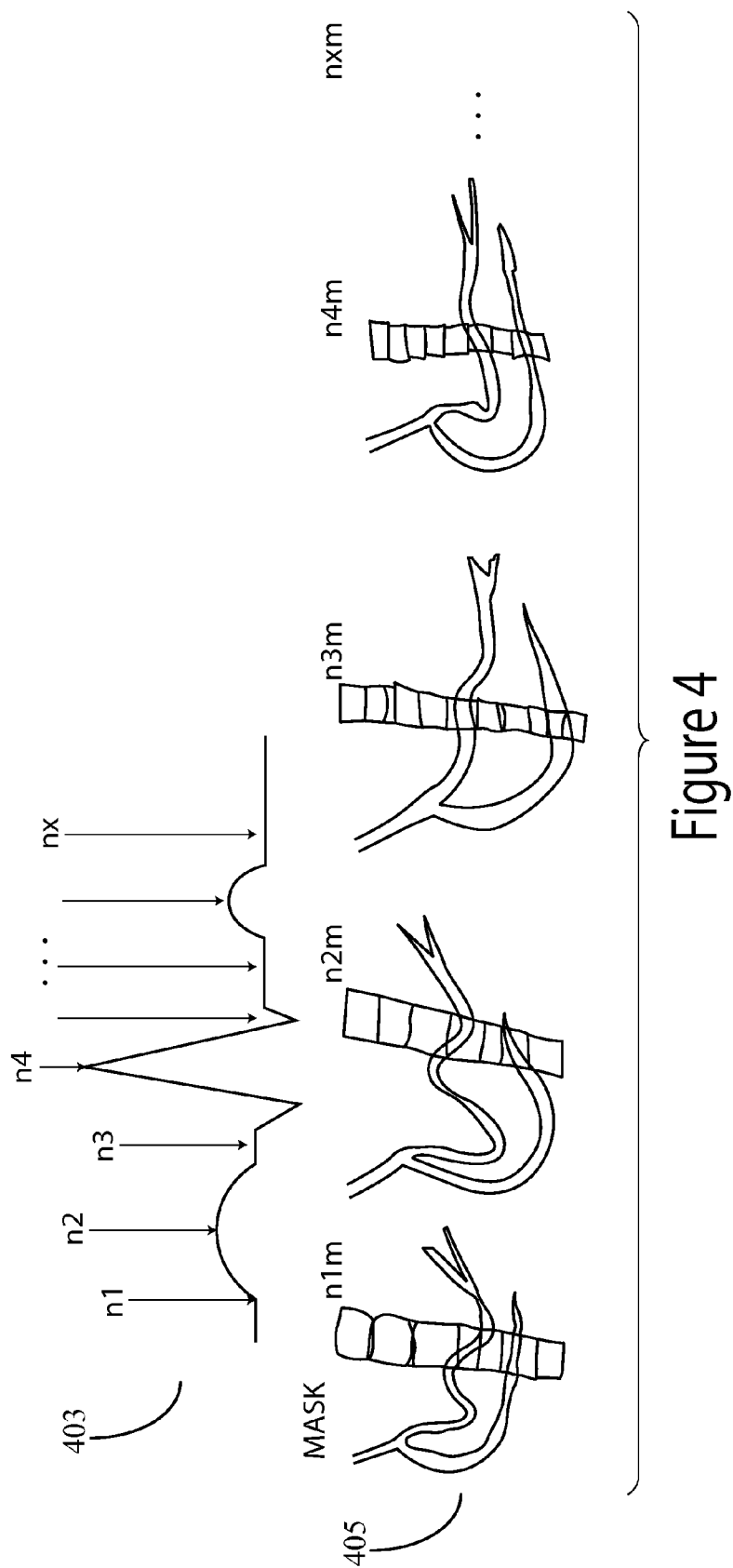
FIGS. 4-6 illustrate acquisition and subtraction of mask and contrast enhanced images to provide DSA images enhancing vessel visualization, according to invention principles.
Figure 5:
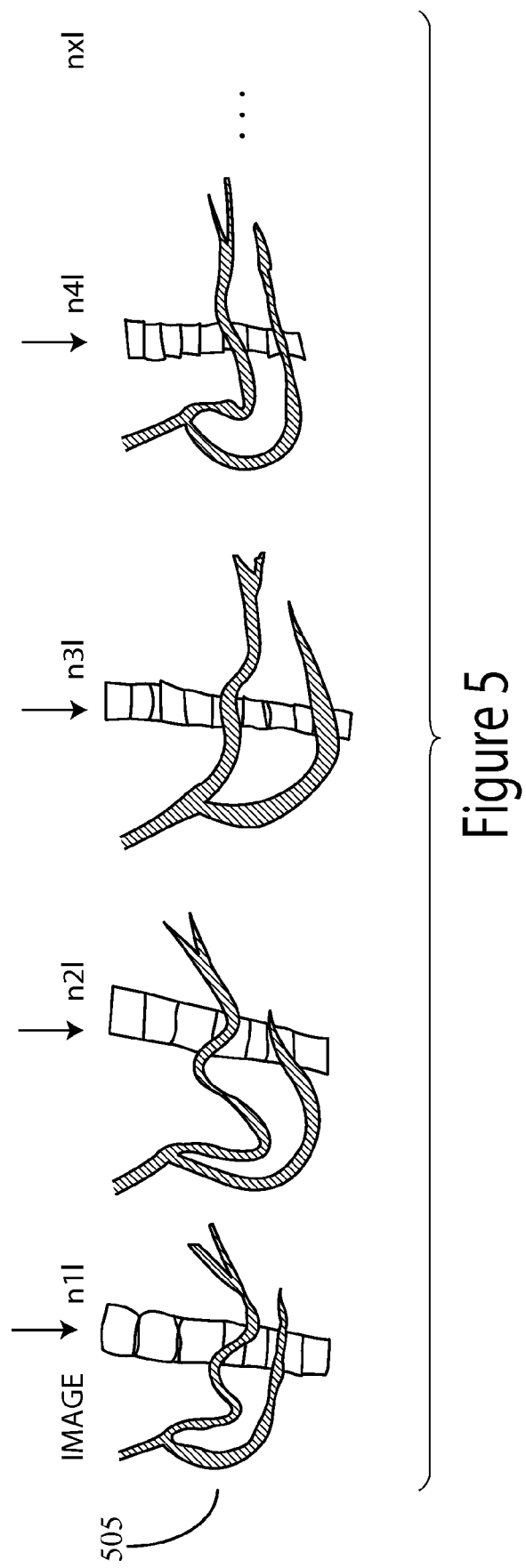
Figure 6:
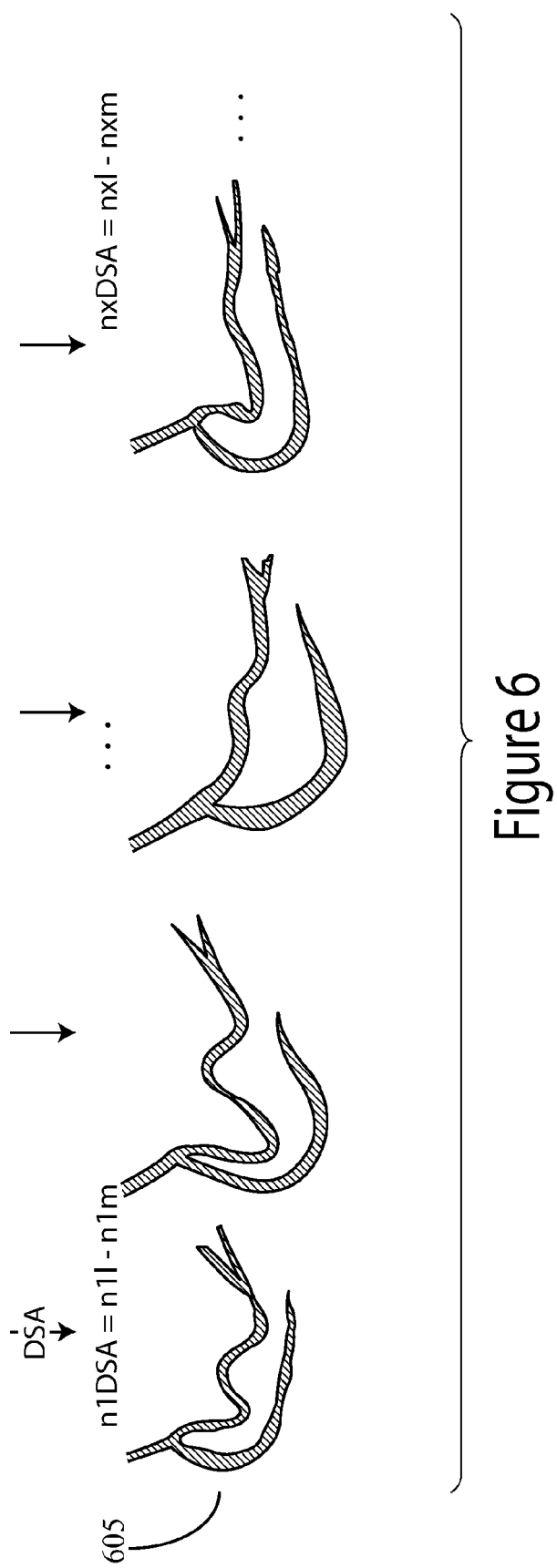

FIGS. 4-6 illustrate acquisition and subtraction of mask and contrast enhanced images to provide DSA images enhancing vessel visualization. System 10 analyzes an acquired ECG signal by identifying PQRST waves for each heart cycle. ECG data for one or more typical heart cycles is acquired for corresponding acquired image frames. FIG. 4 heart cycle (PQRST wave) 403 (see also FIG. 2) is divided into n segments (segments n1, n2, n3, n4 . . . nx) and a corresponding image frame of each segment of the heart cycle is identified and used as a mask frame (mask images n1*m*, n2*m*, n3*m*, n4*m* . . . nxm 405) for use in performing coronary vessel DSA imaging. In one embodiment, for example, mask images are selected from acquired images at 10% (or another portion) intervals of a heart cycle and used as mask image frames for performing coronary DSA image.

FIG. 5 illustrates acquisition by system 10 of images of coronary vessels in the presence of a contrast agent following injection of the agent into the coronary heart vessels. Specifically, images are acquired for a time duration encompassing the desired number of heart cycles and concurrently with acquisition of ECG data. System 10 analyzes the acquired ECG data obtained during the image acquisition time period and identifies PQRST waveform portions and identifies and marks (with tags) corresponding acquired image frames n1I, n2I, n3I, n4I . . . nxI 505 so that mask images and corresponding contrast agent images are identified for the same heart cycle segment. In one embodiment, system 10 synchronizes acquisition of images over the n segments in response to ECG signal data so the mask images and corresponding contrast agent images are acquired at the same corresponding points within a heart cycle. System 10 synchronizes the mask frames with the images that contain the contrast agent by synchronizing the heart cycle of the contrast agent images with corresponding mask frames so that a mask frame and corresponding contrast agent frame are acquired at the same cycle point within a heart beats cycle.

System 10 generates DSA images by subtracting the mask images from corresponding contrast agent images e.g., n1DSA=n1I−n1*m* . . . nxDSA=nxI−nxm, as illustrated in FIG. 6. The resulting DSA images 605 show coronary vessels with background detail removed to enhance visualization of the vessels and are output for presentation to a user on display 19 (FIG. 1) and also for storage. Vessels containing contrast agent are displayed as the result of subtraction. The system advantageously provides DSA images for coronary imaging studies and is applicable for use in image acquisition or fluoroscopy in cardiology and angiography for coronary vessels or any moving vessel in the body.

FIG. 7 shows a flowchart of a process used by image data subtraction system 10 (FIG. 1) for enhancing visualization of vessels subject to movement. In step 712 following the start at step 711, interface 36 receives an electrical signal (e.g., an ECG signal) representing a heart cycle electrical waveform occurring over a multiple heart cycles. Imaging system 25 in step 715 acquires data representing a first image set comprising multiple temporally sequential individual mask images of vessels of a portion of patient anatomy during the multiple heart cycles in the absence of a contrast agent. The portion of patient anatomy comprises a heart and the vessels comprise coronary vessels In step 717 imaging system 25 acquires data representing a second image set comprising multiple temporally sequential individual contrast enhanced images of vessels of the portion of patient anatomy during the multiple heart cycles in the presence of a contrast agent. In one embodiment, imaging system 25 acquires the temporally sequential individual mask images and individual contrast enhanced images of vessels of the portion of patient anatomy substantially at intervals during the multiple heart cycles synchronized with the electrical signal. Specifically, the synchronization signal triggers image acquisition at predetermined intervals during the multiple heart cycles and synchronized with the electrical signal and user interface 26 enables a user to select the predetermined intervals.

Image data processor 29 in step 723 automatically uses the electrical signal to identify temporally corresponding pairs of images comprising a mask image and a contrast enhanced image acquired substantially at a same point within a heart cycle. For the corresponding pairs, image data processor 29 in step 726 automatically subtracts data representing a mask image of a corresponding pair from a contrast enhanced image of the corresponding pair, to provide multiple subtracted images providing enhanced visualization of vessels. Display processor 15 in step 729 processes data representing the subtracted images for presentation on display 19. The process of FIG. 7 terminates at step 731.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system performs Digital Subtraction Angiography of coronary vessels automatically using an electrical signal to identify and subtract temporally corresponding pairs of images comprising a mask image and a contrast enhanced image acquired substantially at a same point within a heart cycle to provide clear, motion artifact free images of blood vessels of the heart. Further, the processes and applications may, in alternative embodiments, be located on one or more (e.g., distributed) processing devices on a network linking the units of FIG. 1. Any of the functions and steps provided in FIGS. 1-7 may be implemented in hardware, software or a combination of both.

What is claimed is:

1. An image data subtraction system to enhance visualization of vessels subject to movement, comprising:
    an interface for receiving an electrical signal representing a heart cycle electrical waveform occurring over a plurality of heart cycles;
    an imaging system for,
    acquiring data representing a first image set comprising a plurality of temporally sequential individual mask images of vessels of a portion of patient anatomy during said plurality of heart cycles in the absence of a contrast agent, and
    acquiring data representing a second image set comprising a plurality of temporally sequential individual contrast enhanced images of vessels of said portion of patient anatomy during said plurality of heart cycles in the presence of a contrast agent, wherein each individual mask image of the first image set is acquired at one of multiple segments within the heart cycle and each contrast enhanced image of the second image set is acquired at one of the same segments within the heart cycle; and
    an image data processor for automatically,
    using said electrical signal to identify corresponding pairs of images, wherein each of the corresponding pairs comprises a mask image and a contrast enhanced image acquired at a same segment within the heart cycle, and
    for each of said corresponding pairs, subtracting data representing a mask image of a corresponding pair from a contrast enhanced image of said corresponding pair, to provide a plurality of subtracted images providing enhanced visualization of vessels.

2. A system according to claim 1, wherein
said vessels are Coronary vessels.

3. A system according to claim 1, wherein
said imaging system acquires said individual mask images in response to a synchronization signal triggering image acquisition at predetermined segments during the heart cycle and synchronized with said electrical signal.

4. A system according to claim 1, wherein
said portion of patient anatomy comprises a heart and said vessels comprise coronary vessels.

5. A system according to claim 1, including
a display processor for processing data representing said subtracted images for display.

6. A system according to claim 1, wherein
said electrical signal is an ECG signal.

7. An image data subtraction system to enhance visualization of vessels subject to movement, comprising:
    an interface for receiving an electrical signal representing a heart cycle electrical waveform during a plurality of heart cycles;
    an imaging system for,
    acquiring data representing a first image set in the absence of a contrast agent and comprising a plurality of temporally sequential individual mask images of vessels of a portion of patient anatomy, wherein each individual mask image of the first image set is acquired at one of multiple segments within a heart cycle based on said electrical signal, and acquiring data representing a second image set in the presence of a contrast agent and comprising a plurality of temporally sequential individual contrast enhanced images of vessels of said portion of patient anatomy, wherein each contrast enhanced image of the second image set is acquired at one of the same multiple segments within the heart cycle based on said electrical signal; and an image data processor for automatically, identifying corresponding pairs of images, wherein each of the corresponding pairs comprises a mask image and a contrast enhanced image acquired at a same segment, and for each of said corresponding pairs, subtracting data representing a mask image of a corresponding pair from a contrast enhanced image of said corresponding pair, to provide a plurality of subtracted images providing enhanced visualization of vessels.

8. A system according to claim 7, wherein said imaging system acquires said individual mask images and said contrast enhanced images in response to a synchronization signal triggering image acquisition at predetermined segments during said at least one heart cycle and synchronized with said electrical signal.

9. A system according to claim 8, including a user interface enabling a user to select said predetermined segments.

10. A method for image data subtraction to enhance visualization of vessels subject to movement, comprising the activities of:

receiving an electrical signal representing a heart cycle electrical waveform occurring over a plurality of heart cycles;

acquiring data representing a first image set comprising a plurality of temporally sequential individual mask images of vessels of a portion of patient anatomy, each individual mask image acquired at one of multiple segments within a heart cycle in the absence of a contrast agent;

synchronizing, in response to the electrical signal, acquisition of data representing a second image set comprising a plurality of temporally sequential individual contrast enhanced images of vessels of said portion of patient anatomy, each contrast enhanced image acquired at one of the same multiple segments within the heart cycle in the presence of a contrast agent;

automatically using said electrical signal to identify corresponding pairs of images, wherein each corresponding pair comprises a mask image and a contrast enhanced image acquired at a same segment within the heart cycle; and for each of said corresponding pairs, automatically subtracting data representing a mask image of a corresponding pair from a contrast enhanced image of said corresponding pair, to provide a plurality of subtracted images providing enhanced visualization of vessels.

11. A method according to claim 10, further comprising triggering, via a synchronization signal, the acquisition of the data representing the first image set.

* * * * *